United States Patent [19]

Doucette

[11] Patent Number: 5,060,387
[45] Date of Patent: Oct. 29, 1991

[54] BLADE HANDLE

[75] Inventor: Thomas H. Doucette, West Milford, N.J.

[73] Assignee: Becton, Dickinson and Company, Franklin Lakes, N.J.

[21] Appl. No.: 612,356

[22] Filed: Nov. 13, 1990

[51] Int. Cl.⁵ .............................................. B26B 1/00
[52] U.S. Cl. ...................................... 30/330; 30/337; 30/339; 606/167
[58] Field of Search ................ 30/329, 330, 331, 337, 30/339; 606/167

[56] References Cited

U.S. PATENT DOCUMENTS

| Re. 30,733 | 9/1981 | Quenot | 30/162 |
|---|---|---|---|
| 576,648 | 2/1897 | Autenrieth . | |
| 881,731 | 3/1908 | Snow . | |
| 977,889 | 12/1910 | Levinsohn . | |
| 1,330,030 | 2/1920 | Parker . | |
| 1,554,083 | 9/1925 | Goldman | 606/167 |
| 1,823,001 | 9/1931 | Rassier | 30/331 |
| 1,914,153 | 6/1933 | Ogden . | |
| 2,039,443 | 5/1936 | Ogden | 30/337 |
| 2,245,096 | 6/1941 | Penney . | |
| 2,463,682 | 3/1949 | Doniger | 30/331 |
| 2,464,206 | 3/1949 | Becker . | |
| 2,478,668 | 8/1949 | Shepard et al. | 30/339 |
| 2,637,105 | 5/1953 | Forst | 30/330 |
| 2,662,287 | 12/1953 | Ferguson . | |
| 2,708,313 | 5/1955 | Steele | 30/339 |
| 3,084,434 | 4/1963 | Hitchcock . | |
| 3,255,523 | 6/1966 | Robertson et al. . | |
| 3,262,205 | 7/1966 | Arden . | |
| 3,383,763 | 5/1968 | Strandfors . | |
| 3,802,077 | 4/1974 | Averitt | 30/339 |
| 3,906,625 | 9/1975 | Gringer | 30/125 |
| 3,906,626 | 9/1975 | Riuli | 30/339 |
| 4,005,525 | 2/1977 | Gringer | 30/125 |
| 4,100,677 | 7/1978 | Jeff | 30/321 |
| 4,103,421 | 8/1978 | Quenot | 30/162 |
| 4,223,737 | 11/1980 | Poehlmann | 30/335 |
| 4,312,128 | 1/1982 | Olsen | 30/157 |
| 4,509,260 | 4/1985 | Gringer | 30/162 |
| 4,575,940 | 3/1986 | Wenzel | 30/339 |
| 4,617,738 | 10/1986 | Kopacz | 30/339 |
| 4,646,440 | 3/1987 | Decker | 30/339 |
| 4,660,287 | 4/1987 | Decker | 30/339 |
| 4,813,132 | 3/1989 | Castelluzzo | 30/162 |
| 4,922,614 | 5/1990 | Machida | 606/167 |
| 4,941,260 | 7/1990 | Castelluzzo | 30/162 |

FOREIGN PATENT DOCUMENTS 713101  8/1954  United Kingdom ................. 30/330

Primary Examiner—Mark Rosenbaum
Assistant Examiner—Hwei-Siu Payer
Attorney, Agent, or Firm—Robert P. Grindle

[57] ABSTRACT

A handle is provided for blades, and particularly surgical blades, which allows simple insertion sequentially of a plurality of blades, and closure to a locked postion of the blade, upon insertion. The two parts of the handle pivot relative to one another in the same longitudinal plane around a pivot positioned adjacent the blade position. This allows a relatively long handle portion for gripping the device for ejecting the blade, using the thumb or finger of the same hand for opening the holder for ejection single-handedly. The gripping portion of the handle has adjacent to the blade portion thereof a boss which conforms to the opening in the blade tang. Closure causes the movble portion of the handle to cover the boss and the blade tang in a wedging action preventing movement of the blade relative to the handle in closed position. When opening, the user pushes the movable portion of the handle open while holding the blade and boss of the fixed handle portion facing downward so that the blade falls out of the device, without any touching or movement of any kind, into a sharps collector.

5 Claims, 3 Drawing Sheets

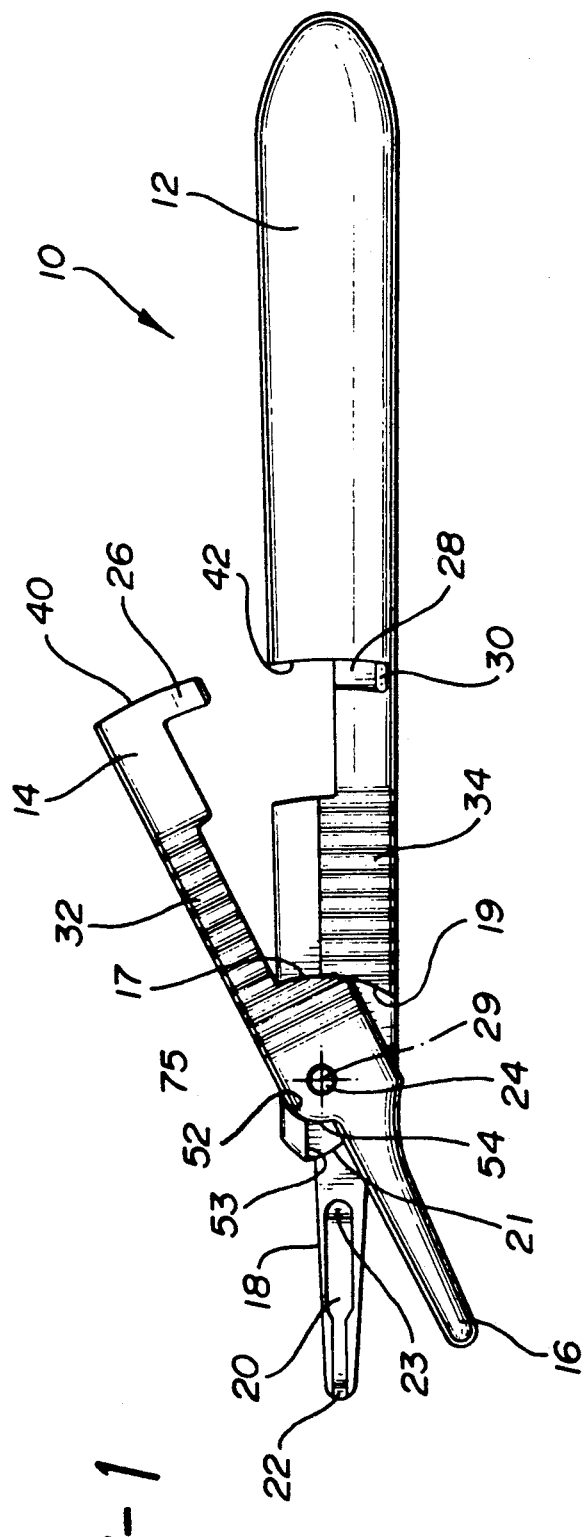
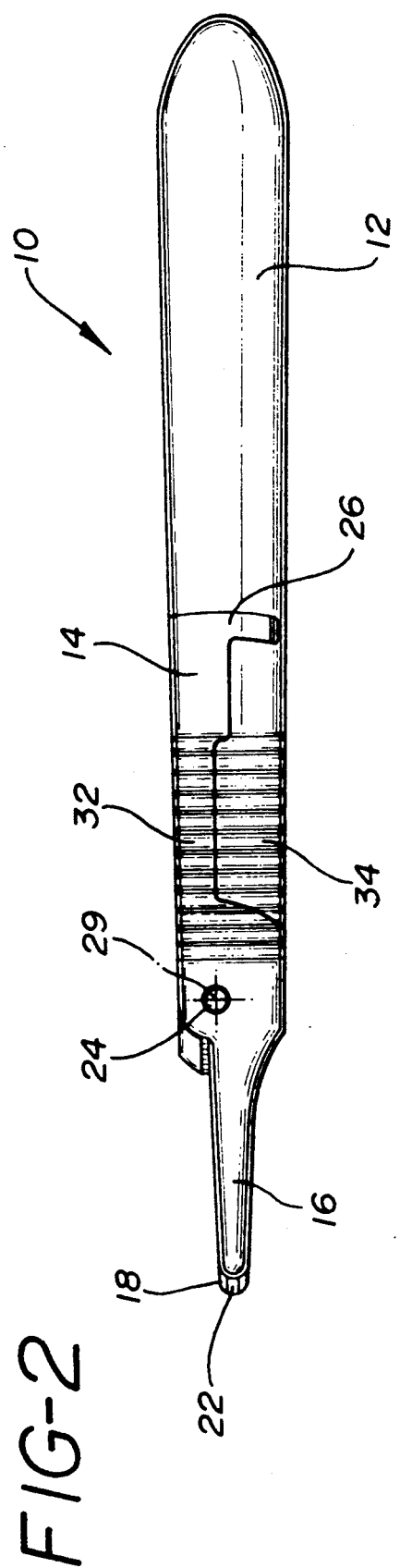
FIG-1
FIG-2

BLADE HANDLE

BACKGROUND AND DESCRIPTION OF THE INVENTION

The present invention relates to a blade handle which allows for the sequential insertion of a plurality of blades for a single use of each blade with subsequent ejection of the blade from the handle for insertion of an additional blade. More particularly, the invention relates to holders for surgical blades and the problems involved in handling contaminated blades in the surgical environment.

As practitioners in the art of surgical blades are aware, AIDS, hepatitis and related contagious diseases present in the blood of patients has made the practice of surgery and medicine, in general, more dangerous than was the case several years ago, simply because one must be extremely careful to avoid contamination of his or her own blood with the blood of an infected patient. For this reason, many devices have been developed for handling instruments to avoid contaminated sharp edges or points which have been contaminated with the blood of infected persons. This is particularly true in the surgical environment where surgical blades are used in great quantity and must be disposed of without being touched, if possible and certainly without the user being cut or having his or her skin punctured in any way.

Thus, it is important to be able to remove a blade from a holder for the blade, after use, without the user having to actually touch the blade, if possible. If it is necessary to touch the blade, then it is appropriate to touch only the tang portion of the blade and avoid any contact with the sharp edge. It is to this environment that the present invention is directed.

Many arrangements have been developed to obviate the problems discussed above, and to provide blade holders which will hold the blade precisely in the position desired, which will provide ease of insertion so that the user does not cut themselves prior to any use of the blade and/or holder, and that the blade is firmly held against any wobbling or movement in the handle, which would reduce the effectiveness of any surgery being performed with such a blade.

Arrangements have been provided in the past wherein elongated blade holders have been provided of the kind discussed here wherein the two parts of the holder pivot relative to each other for insertion of the blade into the holder and for holding the blade in place. These arrangements have a pivot axis at one end of the two parts forming the holder. With such an arrangement, the user cannot handle removal of the blade single handedly since it is necessary to use both hands for handling the two pivoting parts. Representative of such arrangements are U.S. Pat. No. 2,245,096 and U.S. Pat. No. 3,906,625. Both of these patents have the pivot axis positioned at the end opposite the end where the blade is inserted.

Other devices of the kind discussed herein include those in which the pivot axis is positioned centrally of the ends of the blade holder. Again, with such arrangements the user must use both hands to manipulate the two parts around the central pivot axis in order to insert and remove the blade. Representative of such prior art patents are U.S. Pat. Nos. 2,478,668 and 2,637,105.

In order to facilitate a single handed operation for surgical blade holders of the kind discussed herein, it is necessary to position the pivot axis adjacent to the position of the blade during use. This enables the user to have a substantially long non pivoting handle portion to grip for opening and closing the device for insertion and ejection of the blade Representative of such arrangements are U.S. Pat. Nos. 2,039,443 and 1,914,153. Both of these patents use a separate rotating ejector arrangement which pivots adjacent to the blade for causing the blade to become "unwedged" from its use position for removal of the blade. However, the ejector cams the blade only partially out of its holder arrangement. The user must, after this camming action, grip the blade for final removal from the handle thus risking a cut from the contaminated blade.

With this invention, by contrast, a blade holder is provided for surgical blades which allows the user to open and close the device single-handedly. The arrangement includes a fixed non rotating half of the handle which has positioned in the blade position thereof, a boss which is configured to be the same as the opening in the tang of the blade to be inserted. As a further feature, this portion of the holder is indented to the same configuration as the blade tang for easy reception of the blade. For this reason, the blade may be positioned on the fixed portion of the handle of the invention.

At each end of the boss is a cooperating abutment which cooperates with the movable portion of the handle in closed position to capture the blade and lock it in a non movable position for use. Thus, the user, singlehandedly, may close the device and wedge the blade in a fixed position effortlessly.

Once the blade has been used, the user may grip the handle, and with the thumb, move the movable portion of the handle open around the pivot axis which is adjacent to the blade. In doing so, the user also places the boss side of the fixed portion of the handle downwardly. For this reason, once the movable portion of the blade handle has been forced open by the thumb of the user, the blade simply falls out of the device into a container used for such purposes in order to contain contaminated sharp instruments. The user does not touch the blade at all once it has been used and contaminated.

As a further feature of the invention here, the blade holder of the invention is substantially flat and the two portions of the handle pivot relative to one another around a pivot with an axis perpendicular to the flat body of the holder, and positioned adjacent to the position of the blade, as discussed above. Moreover, the two portions pivot around this pivot axis in substantially the same longitudinal plane relative to each other. For this reason, the profile of the holder herein is a simplified flat device easily handled and maneuvered in difficult surgical procedures.

Other objects and advantages of this invention will be apparent from the following description, the accompanying drawings and the appended claims.

DESCRIPTION OF THE DRAWINGS

FIG. 1 is a longitudinal side elevational view of the device of the invention in its open position exposing the boss structure for receiving a surgical blade;

FIG. 2 is the structure of FIG. 1 shown in its closed position;

DETAILED DESCRIPTION OF THE INVENTION

Figure 3:
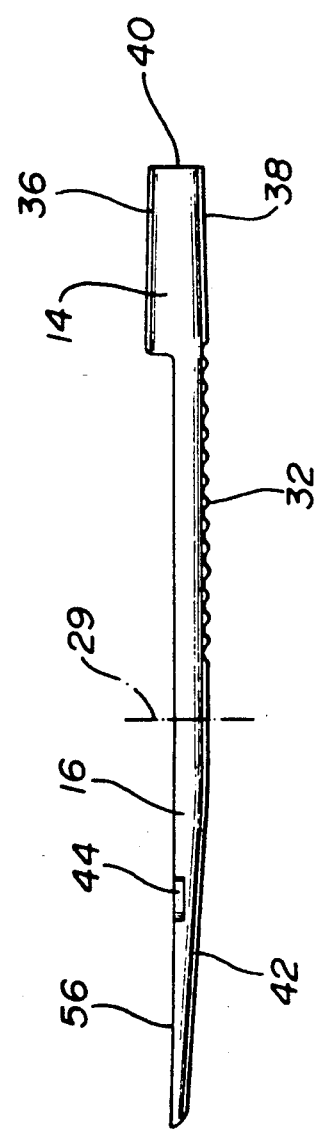
FIG. 3 is a longitudinal end view of the movable handle portion or half of the holder of the invention.

Referring to the drawings in which like reference characters refer to like parts through out the several views thereof, FIG. 1 shows the surgical blade holder of the invention generally designated 10 in its open position, with a fixed handle portion 12 and a rotatable handle portion 14. The two halves 12, 14 rotate relative to each other around a pivot axis 29 with a pivot pin 24 for that purpose. In use, however, the smaller half 14 rotates while the portion 12 is held, and therefore, fixed. The front end portions 16, 18, respectively of the blade holder halves 14, 12, when open, expose a boss 20 having abutments 22, 23 positioned at each end thereof. Boss 20 is configured to be the same as the opening in the tang of a surgical blade for holding the blade in a fixed position once the two portions of the holder 10 are in their closed position as shown in FIG. 2. L-shaped surface 21 (FIG. 6) defines the rear end of the indentation in portion 18 for receiving the blade body.

That is, front end portion 16 of the blade holder movable half moves over the blade itself and the boss 20 to wedge and position both between the two front halves 16, 18 of blade holder 10. When this takes place, of course, the abutments 22, 23 provide a wedging action to hold the blade in a fixed non-moving position. In order to provide the appropriate rotating movement around axis 29, the movable and fixed portions 12, 14 of the blade holder of the invention include cooperating opposed curved surfaces 52, 54 and 17, 19. This allows for rotation of the parts relative to each other without any diversion from the desired controlled rotary movement around pivot axis 29 and rotating pin 24.

As can be seen in FIG. 1, movable rotating portion 14 of handle 10 includes a locking extension 26 which is received in a slot 28 in the fixed portion 12 of handle 10. When extension 26 moves into slot 28, there is positioned at the bottom of extension 26 an abutment 48 (FIG. 4) which cooperates with a depression 30, so that abutment 48 snaps in place locking the two parts against relative rotary movement when not desired.

The two halves 12, 14 also include cooperating curved surfaces 42, 40, respectively, again for maintaining a proper relative movement of the two parts around axis 29 and pivot pin 24. The flat surfaces of the movable and fixed parts 12, 14 of the handle include a plurality of spaced vertical ridges 32, 34 which serve to provide the user with a frictional gripping surface during use of the holder, when a blade is fixed in the holder. While cooperating curved surfaces 52, 54 move relative to each other, in the complete open position of FIG. 1, top surface 75 of the movable part 14 moves against the top edge of surface 52 to serve as a stop against further opening movement.

Figure 4:
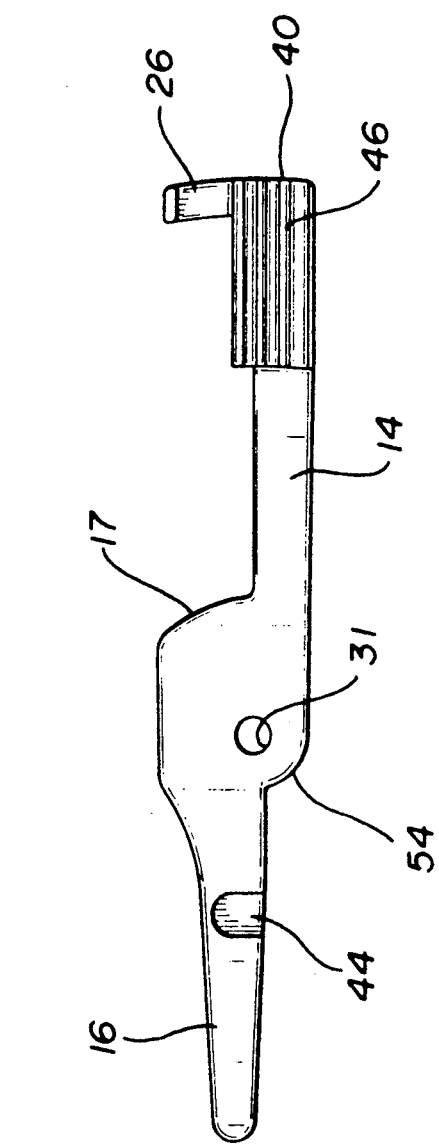
FIG. 4 is a side elevational view of the movable handle portion of the holder of the invention of FIG. 3 showing the opposite side thereof from the showings in FIGS. 1 and 2.

Referring now to FIGS. 3 and 4, these views show the movable portion 14 of the blade holder of the invention separated from the fixed portion thereof for clarity.

As can be seen in FIG. 4, this view is the opposite side of portion 14 from that of FIGS. 1 and 2, and 14 includes a plurality of spaced frictional ridges providing a frictional gripping surface 46. This surface serves to provide the user with a frictional surface for the thumb or finger for the opening movement necessary to open the device to allow the blade to drop from the open blade holder 10. Also shown in the surface 56 of the front end portion of the blade half 14 is an opening 44 which cooperates with the abutment 23 on the fixed portion of the device for maintaining the blade fixed between the cooperating surfaces of the fixed and rotating halves of the holder 10 of the invention.

One of the features of the invention, is the fact that the front portion 16 from the pivot axis 29 as shown in FIG. 3 is bowed slightly along the surface 56 to provide a more firm cooperating wedging action between surface 56 and the cooperating surface on the other half 12 of the blade holder 10 of the invention. Both the fixed and rotating halves of the blade holder of the invention include beveled edges 36, 38, which provide a further ease of holding and/or gripping the holder of the invention during use. Finally, referring to FIG. 3, the movable half 14 of the holder of the invention includes a bore 31 for receiving the rotating pivot pin 24.

Figure 5:
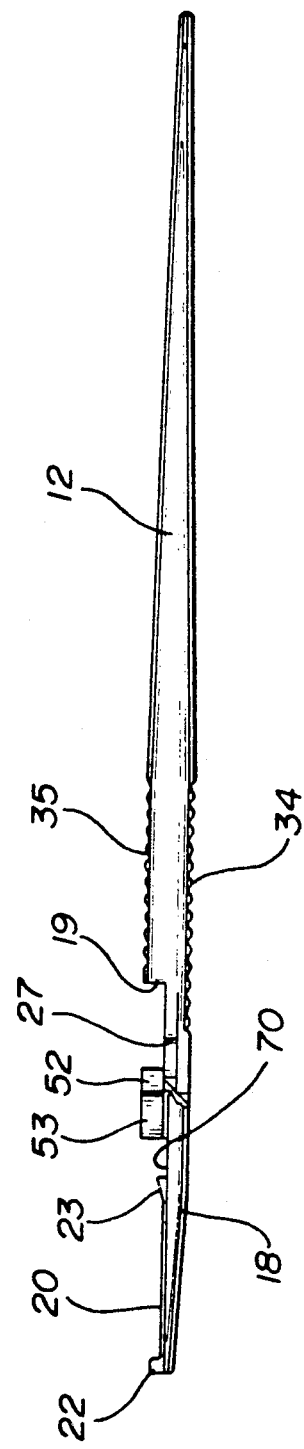
FIG. 5 is a longitudinal end view of the fixed portion or half of the handle of the invention.
Figure 6:
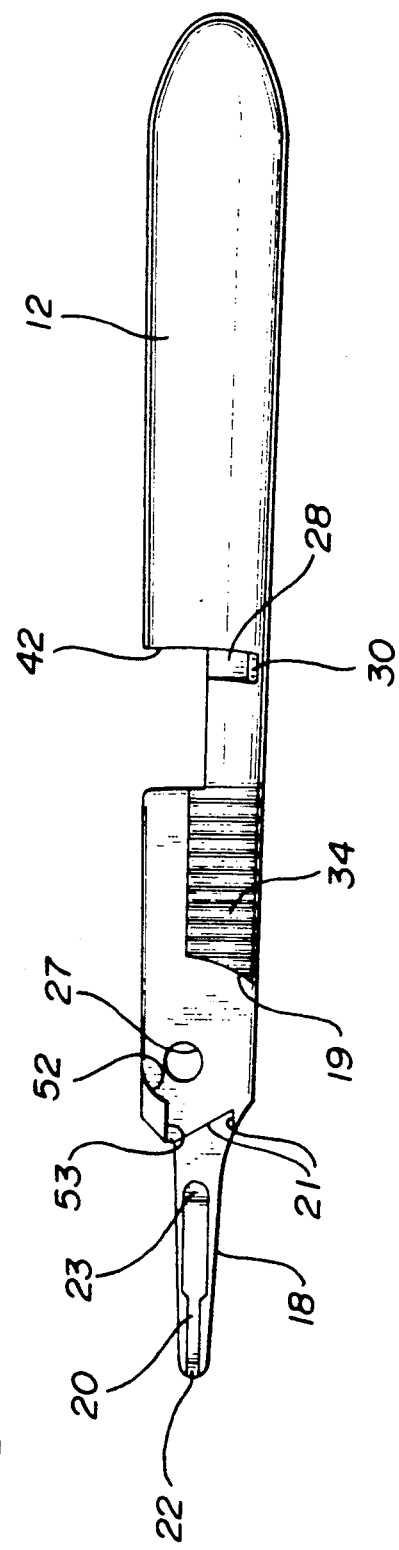
FIG. 6 is a side elevational view of the fixed portion of the handle of the invention of FIG. 5 with the rotating portion removed to show the structure of the fixed portion underneath the rotating portion.

Referring now to FIGS. 5 and 6, the fixed half 12 of the holder 10 of the invention is shown separately from the movable half thereof. As can be seen in FIGS. 5 and 6, bearing surfaces 52, 53 are shown for cooperating with opposed surfaces on the movable half 14 of the blade 10 of the invention. Surface 53 serves as a "stop" for movement to the closed position of the part 14 in cooperation with the movement of the abutment 48 into the opening 30 to cause locking together of the two halves once the blade is in place between the two halves.

Referring now to FIG. 5, the front end portion 18 is bowed slightly as discussed above relative to surface 56 on rotating or movable part 14 so that the surface 70 cooperates with the opposed surface 56 in a wedging action. This bow is not visible to the human eye since the degree of bow is very small in order to provide appropriate movement of the two parts together, and movement in a non locking position when required to eject the blade. Fixed blade holder half 12 also includes a bore 27 for receiving the pivot pin 24 as discussed above. The fixed blade half 12 includes vertical ridges 34, 35, as viewed in FIG. 6, on opposite sides thereof in order to provide the user with a frictional surface for ease of holding the holder 10 during use.

Thus, in order to use the device 10 of the invention, the user grips the rear end of the fixed portion 12 of the invention. For this purpose, as will be readily seen in FIGS. 1 and 2, a large portion of the elongated device of the invention is removed from any movable part so as to provide a gripping surface for opening and closing the device of the invention. Thereafter, the user places their thumb or finger against the surface 46 for providing a force for opening the movable portion 14 of the invention to expose the boss 20 and opposed locking wedges 22, 23 for receiving the opening of a tang of a blade selected for insertion into the holder 10. This force for opening overcomes the cooperating locking surfaces of the parts 48, 30 of the two halves of the holder of the invention.

Once the holder has been opened, the user may place the blade appropriately with the opening of the blade over the boss 20. Then, the user simply moves the movable holder portion 14 so as to cause the abutment 48 to move in position in the opening 30 for locking the two parts together. With this movement, the blade is fixed in place with no "wobbling" in the holder. Then the user may use the holder with the blade in an appropriate desired way.

Subsequent to use, the contaminated blade may be removed readily by the user. This is done simply by, again, holding the rear end of the fixed portion of the device of the invention and placing the thumb or finger against the frictional surface 46 for movement of the rotating portion 14 around pivot axis 29. This force overcomes the locking engagement of cooperating parts 30, 48 and allows the two parts to open to a position as shown in FIG. 1. Thereafter, the user may, if the boss 20 is positioned upwardly, simply turn the holder so that the boss is positioned downwardly and the blade will fall out into a container provided for that purpose.

For this reason, the user's hands are not contaminated by any blood on a blade which has been used in the holder of the invention. There is no required movement on the part of the user of any kind to touch or remove the blade from the holder. It simply falls from the holder when the holder is opened, as discussed above.

Thus, as will be appreciated from the above, there is provided in accordance with this invention a surgical blade holder which is relatively simple and uncomplicated in its construction and easily stamped from a selected material such as stainless steel in a mass production line. The arrangement is such that the user may insert a blade in a very simple manner and, again remove the blade without ever touching the blade if it should be in fact contaminated. It should be understood, of course, that the holder of the invention may be used for blades other than surgical blades. The simplicity of the structure here is such that many uses may be provided with the holder of the type described here. However, it is also important to note that the holder of the invention, regardless of its simplicity, holds the blade in a complete fixed position with no movement in the holder. This allows the user to provide a precise cutting action as desired for the use of the blade being selected.

While the forms of apparatus herein described constitute preferred embodiments of the invention, it is to be understood that the invention is not limited to these precise forms of apparatus, and that changes may be made therein without departing from the scope of the invention which is defined in the appended claims. For example, whereas one form of boss is shown for receiving the opening of a blade, it will be understood that different boss configurations may be selected in order to accommodate the openings in the tang of a variety of different blades. Again, as discussed above, the device of the invention is comprised of two very simple parts which may be readily stamped from a selected material in a mass production line.

What is claimed is:

1. A blade holder, comprising:
   (a) an elongated flat fixed body portion;
   (b) a blade receiving area at one end of said elongated fixed body portion;
   (c) a handle gripping area at the other end of said fixed body portion opposite said blade receiving area;
   (d) a pivot pin on said flat fixed body intermediate the ends thereof adjacent said blade receiving area;
   (e) the axis of said pivot pin being perpendicular to said flat fixed body portion;
   (f) an integral elongated boss on the surface of said blade receiving area for receiving the tang of a blade, said boss being the same shape as the opening in the tang of a blade to be received thereover;
   (g) an abutment extending from each end of said integral elongated boss;
   (h) an elongated flat rotatable body portion having a pivot axis intermediate the ends thereof
   (i) said rotatable body portion rotatable around said pivot axis on said pivot pin from an open position for receiving a blade in said blade receiving area to a closed position locking a blade tank in said blade receiving area;
   (j) said abutments for engaging the cooperating opposed surfaces of said elongated rotatable body portion; and
   (k) cooperating locking means on said flat fixed body portion and said rotatable body portion for locking the tang of a blade in said blade receiving area.

2. The blade holder of claim 1, further comprising
   (a) frictional gripping surfaces on each side of said fixed and rotatable body portions for holding said blade holder during use.

3. The blade holder of claim 1, wherein
   (a) the opposed surfaces of said elongated flat fixed portion and said elongated flat rotatable portion are bowed toward each other in said blade receiving area;
   (b) whereby in said locked position the said opposed bowed surfaces serve to hold a blade therein fixed against any movement relative to said blade holder.

4. A blade holder, comprising
   (a) an elongated flat fixed body portion;
   (b) a blade receiving area at one end of said elongated flat fixed body portion;
   (c) a handle gripping area at the other end of said flat fixed body portion opposite said blade receiving area;
   (d) a pivot pin on said flat fixed body portion intermediate the ends thereof adjacent said blade receiving area;
   (e) the axis of said pivot pin being perpendicular to said flat fixed body portion;
   (f) a boss on the surface of said blade receiving area for receiving the tang of a blade, said boss being the same shape as the opening in the tang of a blade to be received thereover;
   (g) an elongated flat rotatable body portion having a pivot axis intermediate the ends thereof;
   (h) said rotatable body portion rotatable around said pivot axis on said pivot pin from an open position for receiving a blade in said blade receiving area to a closed position locking a blade tang in said blade receiving area; and
   (i) cooperating locking means on said flat fixed body portion and said rotatable body portion for locking the tang of a blade in said blade receiving area, said cooperating locking means including
      (1) a curved slot on said elongated fixed body portion;
      (2) an indentation at the end of said curved slot;
      (3) a curved extension on said rotatable body portion at the other end thereof opposite said blade receiving area; and
      (4) a locking abutment on the end of said curved extension for extending into said indentation at this end of said curved slot.

5. The blade holder of claim 4, further comprising (a) a frictional gripping surface on the side of said flat rotatable body portion opposite said curved locking extension for urging said flat rotatable body portion to the open position; and
(b) said frictional gripping surface having ribs oriented parallel to the longitudinal extent of said rotatable body portion.

* * * * *